United States Patent
Old

(10) Patent No.: US 8,377,984 B2
(45) Date of Patent: Feb. 19, 2013

(54) SUBSTITUTED GAMMA LACTAMS AS THERAPEUTIC AGENTS

(75) Inventor: David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 511 days.

(21) Appl. No.: 12/354,919

(22) Filed: Jan. 16, 2009

(65) Prior Publication Data

US 2009/0192159 A1  Jul. 30, 2009

Related U.S. Application Data

(60) Provisional application No. 61/024,295, filed on Jan. 29, 2008.

(51) Int. Cl.
*A61K 31/40* (2006.01)
*C07D 207/04* (2006.01)

(52) U.S. Cl. ........................................ 514/422; 548/543

(58) Field of Classification Search .................. 514/422; 548/543
See application file for complete search history.

(56) References Cited

U.S. PATENT DOCUMENTS

| | | | |
|---|---|---|---|
| 7,091,231 B2 | 8/2006 | Donde et al. | |
| 7,473,702 B2* | 1/2009 | Old et al. | 514/422 |
| 7,476,747 B2* | 1/2009 | Old et al. | 548/545 |
| 7,550,502 B2* | 6/2009 | Old et al. | 514/422 |
| 7,592,364 B2* | 9/2009 | Old et al. | 514/422 |
| 7,799,821 B2* | 9/2010 | Donde et al. | 514/422 |
| 7,820,661 B2* | 10/2010 | Old et al. | 514/237.2 |
| 7,879,854 B2* | 2/2011 | Old et al. | 514/237.2 |
| 7,960,381 B2* | 6/2011 | Old et al. | 514/237.2 |
| 7,973,071 B2* | 7/2011 | Old et al. | 514/422 |

FOREIGN PATENT DOCUMENTS

| | | |
|---|---|---|
| WO | WO 2006/098918 A2 | 9/2006 |
| WO | WO 2008/094912 A2 | 8/2008 |

OTHER PUBLICATIONS

Patani, George A. Bioisosterism: A rational approach in drug design. Chem. Rev. 96 (1996) 3147-3176.*
U.S. Appl. No. 60/894,297, filed Mar. 12, 2007.
Silverman, Richard B.; Prodrugs and drug Delivery Systems, Organic Chemistry of Drug Design and Drug Action, 2d Ed., Elsevier Academic Press: Amsterdam, 2004, pp. 496-557.

* cited by examiner

*Primary Examiner* — Rebecca Anderson
*Assistant Examiner* — Samantha Shterengarts
(74) *Attorney, Agent, or Firm* — John Wurst; Kevin J. Forrestal

(57) ABSTRACT

Disclosed herein is a compound represented by the formula:

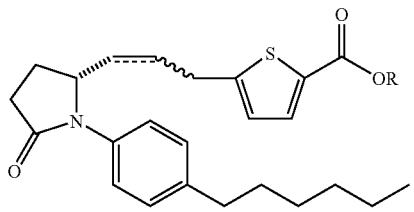

Methods, compositions, and medicaments related to these compounds are also disclosed.

8 Claims, No Drawings

SUBSTITUTED GAMMA LACTAMS AS THERAPEUTIC AGENTS

RELATED APPLICATION

This application claims the benefit of priority under 35 U.S.C. §120 of U.S. Provisional Application Ser. No. 61/024,295 filed on Jan. 29, 2008, the disclosure of which is hereby incorporated in its entirety herein by reference.

DESCRIPTION OF RELATED ART

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

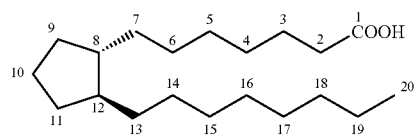

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

DESCRIPTION OF THE INVENTION

A compound is disclosed herein of the formula:

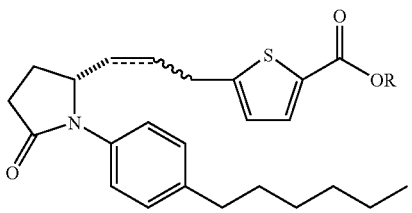

wherein a dashed line represents the presence or absence of a bond, and

R is H, methyl, ethyl, propyl, isopropyl, —$(CH_2)_2OH$ or

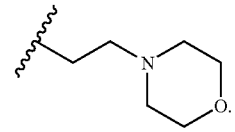 [SMILES: *CCN1CCOCC1]

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. These compounds are also useful for growing hair, including one or more of: increasing the number of individual hairs, increasing the length of individual hairs, and increasing the width or thickness of individual hairs. These compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231). Alternatively, these same compositions could be administered to an area of a mammal in need of hair growth or improvement of the appearance of hair.

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press: Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —$CO_2(CH_2)_2OH$,

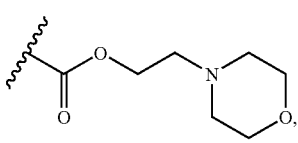

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

Since a dashed line indicates the presence or absence of a bond, compounds according to any one of the structures below are contemplated.

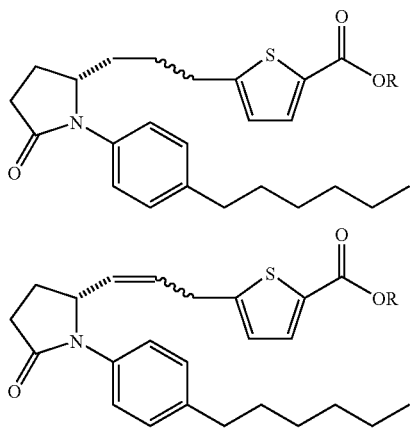

Since R is H, methyl, ethyl, propyl, isopropyl, —$CO_2$($CH_2$)$_2$OH or

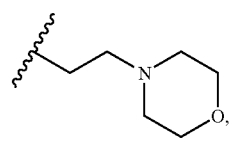

compounds according to any one of the structures below are contemplated.

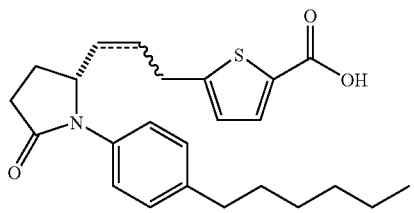

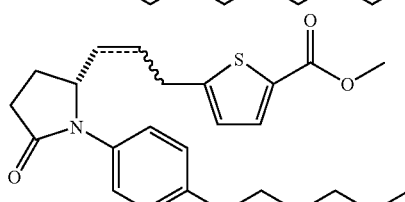

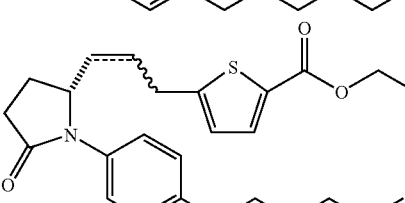

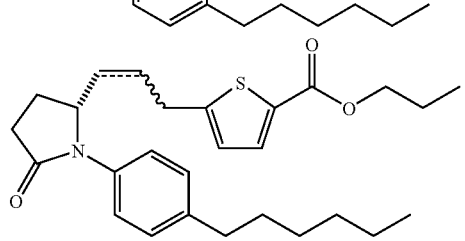

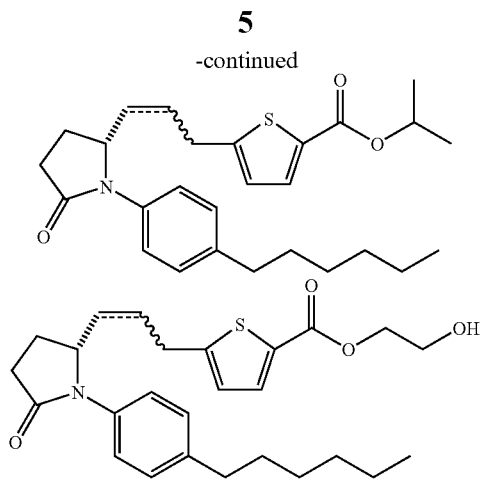
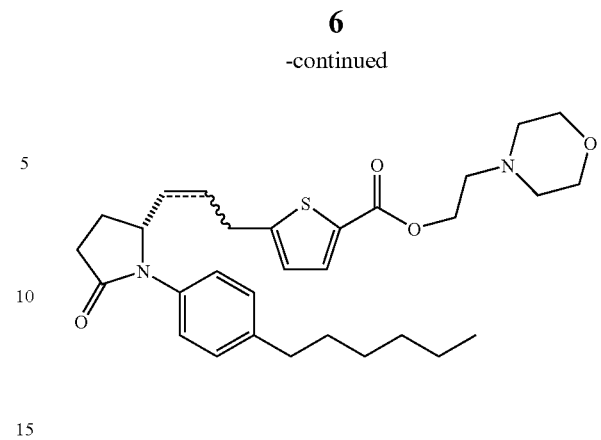
Synthetic Methods
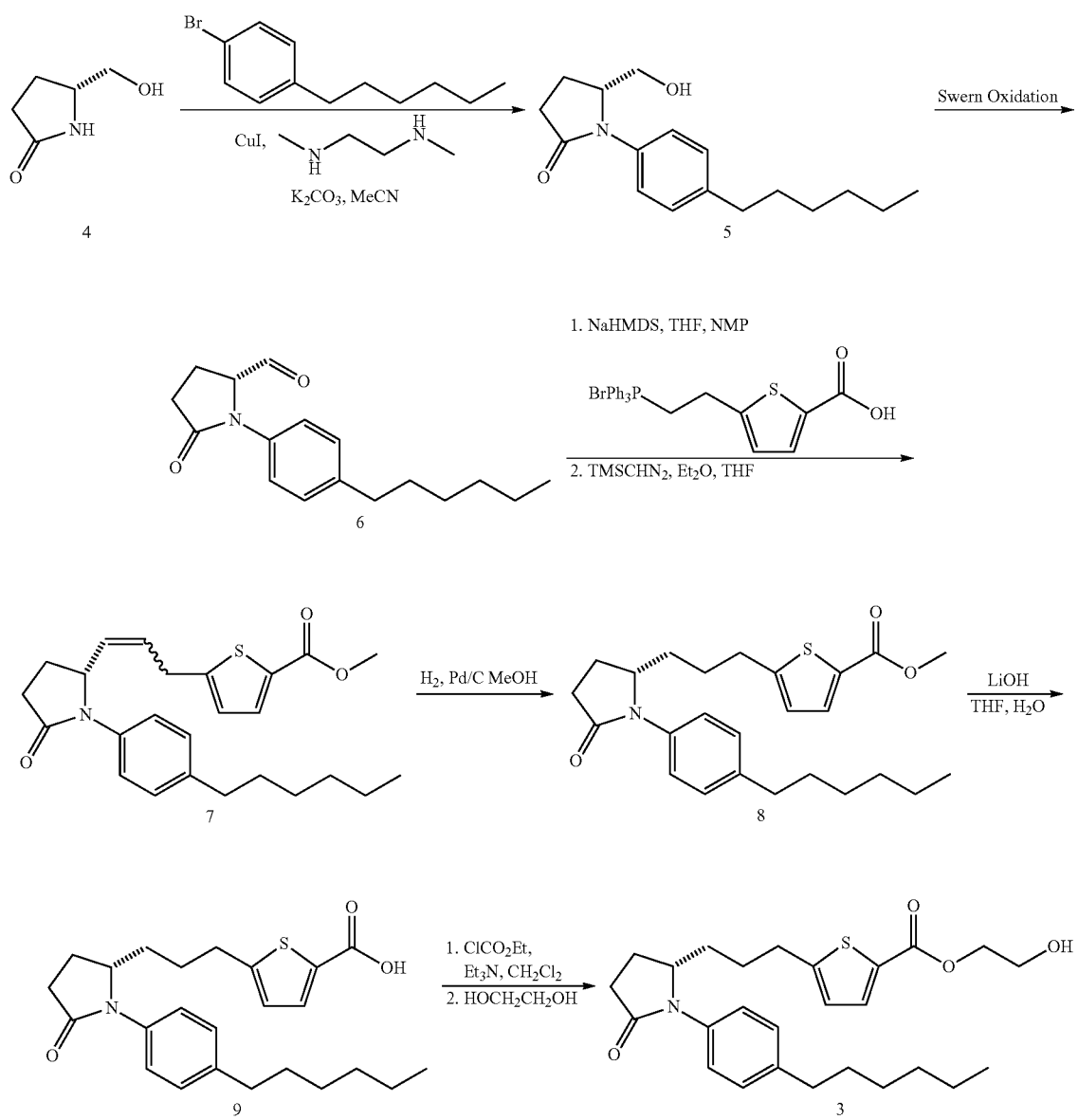

(S)-5-(3-(1-(4-hexylphenyl)-5-oxopyrrolidin-2-yl) propyl)thiophene-2-carboxylic acid 2-hydroxyethyl ester (3)

Step 1. Arylation of 4 to Give 5

Copper (I) iodide (106 mg, 0.56 mmol) and N,N'-dimethylethylenediamine (120 μL, 1.11 mmol) were added in rapid succession to a mixture of (R)-5-(hydroxymethyl)pyrrolidin-2-one (4, 776 mg, 6.74 mmol), 1-bromo-4-n-hexylbenzene (1.34 g, 5.56 mmol) and potassium carbonate (1.53 g, 11.07 mmol) in acetonitrile (12.6 mL). The mixture was heated at reflux. After 3 days, the mixture was cooled to room temperature, diluted with EtOAc (100 mL), and filtered through celite, washing with excess EtOAc. The filtrate was concentrated in vacuo. Purification of the residue by chromatography on 120 g silica gel (hexanes→EtOAc, gradient) afforded 960 mg (63%) of compound 5.

Step 2. Oxidation of 5 to Give 6

DMSO (315 μL, 4.44 mmol) was added to a −78° C. solution of oxalyl chloride (1.1 mL of a 2.0 M solution in $CH_2Cl_2$, 2.2 mmol) and $CH_2Cl_2$ (15 mL). After 15 min at −78° C., a solution of 5 (489 mg, 1.78 mmol) in $CH_2Cl_2$ (15 mL) was added via cannula. After 15 min at −78° C., triethylamine (1.98 mL, 14.2 mmol) was added dropwise and the mixture was allowed to warm to 0° C. After 45 min at 0° C., the reaction was diluted with $CH_2Cl_2$ (50 mL) and saturated aqueous $NaHCO_3$ (100 mL) was added. The phases were separated and the aqueous phase was extracted with $CH_2Cl_2$ (2×100 mL). The combined organic phase was dried ($Na_2SO_4$), filtered and concentrated in vacuo. The crude residue, compound 6, was used in the next step without further purification.

Step 3. Wittig Reaction of 6 and Alkylation to Give 7

Sodium bis(trimethylsilyl)amide (3.60 mL of a 1.0 M solution in THF, 3.60 mmol) was added to a solution of [2-(5-carboxy-thiophen-2-yl)-ethyl]-triphenylphosphonium bromide (see U.S. Provisional Patent Application No. 60/894,267, filed Mar. 12, 2007, incorporated by reference herein, 895 mg, 1.80 mmol) in 1-methyl-2-pyrrolidinone (NMP, 3.6 mL) at 0° C. The resulting deep red solution was stirred at 0° C. for 30 min then was cooled to −20° C. A solution of 6 (~1.78 mmol crude) in THF (3.6 mL) was added to the red ylide solution by cannula. After 30 min at −20° C., the mixture was allowed to warm to 0° C. After 30 min at 0° C. the reaction was quenched by the addition of saturated aqueous $NH_4Cl$ (50 mL) and extracted with EtOAc (3×100 mL). The combined organic phase was dried ($Na_2SO_4$), filtered and concentrated in vacuo. The crude residue dissolved in THF (18 mL) and cooled to 0° C. (Trimethylsilyl)diazomethane (4.4 mL of a 2.0 M solution in $Et_2O$, 8.8 mmol) was added and the mixture was allowed to warm to room temperature. After 30 min at room temperature the mixture was concentrated in vacuo. Purification of the residue by chromatography on 80 g silica gel (hexanes→EtOAc, gradient) afforded 256 mg (34% from 5) of compound 7.

Step 4. Hydrogenation of 7 to Give 8

Palladium on carbon (10 wt. %, 53 mg) was added to a solution of 7 (213 mg, 0.50 mmol) in MeOH (5.0 mL). A hydrogen atmosphere was established by evacuating and refilling with hydrogen (5×) and the mixture was stirred under a balloon of hydrogen. After 42 h, the reaction mixture was filtered through celite, washing with excess MeOH. The filtrate was concentrated in vacuo to afford 182 mg (85%) of 8.

Step 5. Saponification of 8 to Give 9

Lithium hydroxide (2.1 mL of a 1.0 M solution in water, 2.1 mmol) was added to a solution of 8 (182 mg, 0.42 mmol) in THF (4.2 mL) and the mixture was heated at 40° C. After 18 h at 40° C., the mixture was cooled concentrated in vacuo. The residue was diluted with water (5 mL) and acidified with 1 N aqueous HCl (3 mL). The mixture was extracted with EtOAc (3×30 mL). The combined extracts were washed with brine (20 mL), dried ($Na_2SO_4$), filtered and concentrated in vacuo. Purification of the crude residue by chromatography on 12 g silica gel ($CH_2Cl_2$→15% MeOH/$CH_2Cl_2$, gradient) afforded 140 mg (80%) of 9.

Step 6. Esterification of 9 to Give 3

Triethylamine (60 μL, 0.43 mmol) and ethyl chloroformate (21 μL, 0.22 mmol) were added sequentially to a solution of 9 (60 mg, 0.145 mmol) in $CH_2Cl_2$ (2 mL) at 0° C. The mixture was allowed to warm to rt. After 30 min at rt, ethylene glycol (81 μL, 1.45 mmol) was added. After stirring 3 days at room temperature, the reaction mixture was concentrated under a stream of nitrogen. The residue was diluted with EtOAc (50 mL) and washed with $H_2O$ (2×25 mL) and brine (25 mL). The organic phase was dried ($Na_2SO_4$), filtered and concentrated in vacuo. Purification of the residue by chromatography on 4 g silica gel (hexanes→EtOAc, gradient) afforded 28 mg (42%) of the title compound (3).

In Vivo Data (S)-5-(3-(1-(4-hexylphenyl)-5-oxopyrrolidin-2-yl)propyl)thiophene-2-carboxylic acid 2-hydroxyethyl ester (3) was tested in normotensive dogs at 0.003%, dosing once daily for 5 days. The maximum intraocular pressure (IOP) decrease from baseline was 5.9 mmHg (36%) at 54 h; the maximum ocular surface hyperemia (OSH) score was 1.1 at 74 h. This compound was also tested in laser-induced hypertensive monkeys, using one single day dose. At 0.003%, the maximum IOP decrease from baseline was 17 mmHg (44%) at 6 h.

(S)-5-(3-(1-(4-hexylphenyl)-5-oxopyrrolidin-2-yl)propyl) thiophene-2-carboxylic acid (9) was tested in normotensive dogs at 0.003%, dosing once daily for 5 days. The maximum intraocular pressure (IOP) decrease from baseline was 4.7 mmHg (29%) at 6 h; the maximum ocular surface hyperemia (OSH) score was 1.9 at 76 h. This compound was also tested in laser-induced hypertensive monkeys, using one single day dose. At 0.003%, the maximum IOP decrease from baseline was 9 mmHg (23%) at 6 h.

(S)-5-(3-(1-(4-hexylphenyl)-5-oxopyrrolidin-2-yl)propyl) thiophene-2-carboxylic acid isopropyl ester was tested in normotensive dogs at 0.003%, dosing once daily for 4 days. The maximum intraocular pressure (IOP) decrease from baseline was 3.9 mmHg (24%) at 30 h; the maximum ocular surface hyperemia (OSH) score was 0.7 at 28 h. This compound was also tested in laser-induced hypertensive monkeys, using one single day dose. At 0.003%, the maximum IOP decrease from baseline was 12 mmHg (28%) at 6 h.

| Cmpd# | Structure | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | Ki | hFP | hEP1 | hEP3A | hTP | hIP | hDP |
| 9 | 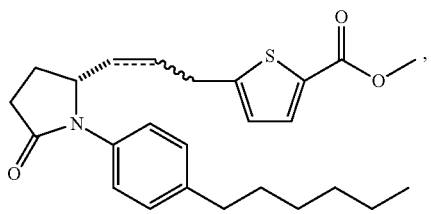 | 5 | 0.5 | 3 | 11281 | 2614 | NA | NA | 1555 | NA | NA | 389 |

What is claimed is:

1. A compound represented by the formula:

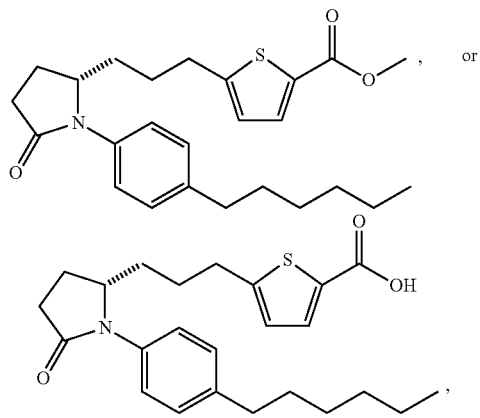

or a pharmaceutically acceptable salt thereof.

2. The compound of claim 1 represented by the formula:

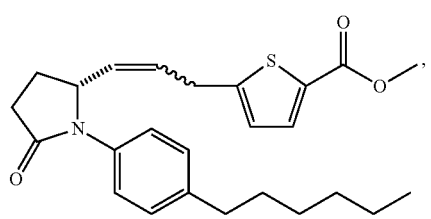 [SMILES: CCCCCCc1ccc(N2C(=O)CC[C@@H]2C=CCc2ccc(C(=O)OC)s2)cc1]

or a pharmaceutically acceptable salt thereof.

3. The compound of claim 1 represented by the formula:

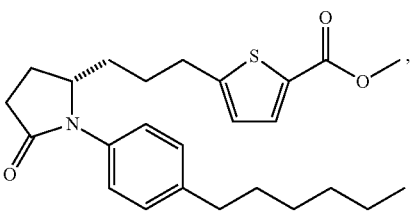 [SMILES: CCCCCCc1ccc(N2C(=O)CC[C@@H]2CCCc2ccc(C(=O)OC)s2)cc1]

or a pharmaceutically acceptable salt thereof.

4. The compound of claim 1 represented by the formula:

or a pharmaceutically acceptable salt thereof.

5. A composition comprising a compound according to claim 1, or a pharmaceutically acceptable salt thereof, wherein said composition is a liquid which is ophthalmically acceptable.

6. A method of treating glaucoma or ocular hypertension comprising administering a compound according to claim 1, or a pharmaceutically acceptable salt thereof, to a mammal in need thereof, wherein said treatment does not encompass the prevention or cure of glaucoma or ocular hypertension.

7. A method of growing hair comprising administering a compound according to claim 1, or a pharmaceutically acceptable salt thereof, to a mammal in need thereof.

8. A method of improving the appearance of hair comprising administering a compound according to claim 1, or a pharmaceutically acceptable salt thereof, to a mammal in need thereof, wherein said appearance is improved by increasing the gloss of hair or changing the color of hair.

* * * * *